United States Patent
Long

(10) Patent No.: US 7,556,627 B2
(45) Date of Patent: Jul. 7, 2009

(54) MUCOSAL ABLATION DEVICE

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 416 days.

(21) Appl. No.: 10/939,726

(22) Filed: Sep. 13, 2004

(65) Prior Publication Data

US 2006/0058781 A1 Mar. 16, 2006

(51) Int. Cl.
*A61B 18/18* (2006.01)

(52) U.S. Cl. ............................. 606/41; 606/46; 606/50; 600/104

(58) Field of Classification Search .................. 606/32, 606/41–52, 1; 600/104, 127, 107; 128/898
See application file for complete search history.

(56) References Cited

U.S. PATENT DOCUMENTS

| | | | |
|---|---|---|---|
| 5,395,327 A | | 3/1995 | Lundquist et al. |
| 5,522,815 A | * | 6/1996 | Durgin et al. ................ 606/50 |
| 5,578,030 A | * | 11/1996 | Levin .......................... 606/39 |
| 5,827,216 A | * | 10/1998 | Igo et al. ...................... 604/21 |
| 5,868,770 A | * | 2/1999 | Rygaard ....................... 606/167 |
| 5,972,013 A | * | 10/1999 | Schmidt ....................... 606/185 |
| 6,022,334 A | | 2/2000 | Lundquist et al. |
| 6,080,175 A | * | 6/2000 | Hogendijk .................. 606/185 |
| 6,086,583 A | | 7/2000 | Ouchi |
| 6,231,518 B1 | * | 5/2001 | Grabek et al. ............... 600/508 |
| 6,394,949 B1 | * | 5/2002 | Crowley et al. ............. 600/127 |
| 6,616,661 B2 | * | 9/2003 | Wellman et al. ............. 606/50 |
| 6,918,908 B2 | * | 7/2005 | Bonner et al. ................ 606/41 |
| 7,066,893 B2 | * | 6/2006 | Hibner et al. ............... 600/566 |
| 7,238,182 B2 | * | 7/2007 | Swoyer et al. ............... 606/41 |
| 2002/0095139 A1 | * | 7/2002 | Keogh et al. ................. 606/1 |
| 2002/0138109 A1 | * | 9/2002 | Keogh et al. ................. 607/9 |
| 2002/0177847 A1 | * | 11/2002 | Long ............................ 606/46 |
| 2002/0183739 A1 | * | 12/2002 | Long ............................ 606/41 |
| 2004/0082859 A1 | * | 4/2004 | Schaer ........................ 600/459 |
| 2004/0087936 A1 | * | 5/2004 | Stern et al. ................... 606/41 |
| 2004/0138527 A1 | * | 7/2004 | Bonner et al. ............... 600/114 |

(Continued)

FOREIGN PATENT DOCUMENTS

WO WO 01/05318 A1 1/2001

(Continued)

OTHER PUBLICATIONS

EPO Search Report dated Apr. 22, 2005 for corresponding patent application, European Patent Application No. EP 03 255 823.1.

*Primary Examiner*—Michael Peffley
*Assistant Examiner*—Victoria W Chen
(74) *Attorney, Agent, or Firm*—Welsh & Flatman LLC

(57) ABSTRACT

A medical device for performing a therapeutic procedure on a patient. The device includes a body that is sized and shaped to engage a working end of an endoscope. The body has a recess therein. The device also includes an electrode positioned on the body and communicative with an energy source for delivering energy to the electrode when performing the Therapeutic procedure on the patient. The device further includes an infection needle positioned in the recess and communicative with a fluid source for delivering fluid to the needle when performing the therapeutic procedure on the patient.

9 Claims, 18 Drawing Sheets

U.S. PATENT DOCUMENTS

| | | | |
|---|---|---|---|
| 2004/0138531 A1* | 7/2004 | Bonner et al. | 600/156 |
| 2004/0215179 A1* | 10/2004 | Swoyer et al. | 606/32 |
| 2004/0260280 A1* | 12/2004 | Sartor | 606/37 |
| 2004/0267326 A1* | 12/2004 | Ocel et al. | 607/9 |
| 2005/0070890 A1* | 3/2005 | Nobis et al. | 606/45 |
| 2005/0070894 A1* | 3/2005 | McClurken | 606/48 |
| 2005/0096638 A1* | 5/2005 | Starkebaum et al. | 606/34 |
| 2005/0096713 A1* | 5/2005 | Starkebaum et al. | 607/100 |
| 2005/0203441 A1* | 9/2005 | Voegele | 600/567 |
| 2005/0222537 A1* | 10/2005 | Dinsmoor et al. | 604/174 |
| 2005/0222563 A1* | 10/2005 | McDaniel et al. | 606/41 |
| 2005/0222646 A1* | 10/2005 | Kroll et al. | 607/72 |
| 2005/0247320 A1* | 11/2005 | Stack et al. | 128/898 |
| 2005/0251208 A1* | 11/2005 | Elmer et al. | 606/232 |
| 2006/0030849 A1* | 2/2006 | Mirizzi et al. | 606/50 |
| 2006/0052769 A1* | 3/2006 | Long | 606/41 |
| 2006/0122583 A1* | 6/2006 | Pesach et al. | 606/7 |

FOREIGN PATENT DOCUMENTS

WO      WO 01/24721 A1     4/2001

* cited by examiner

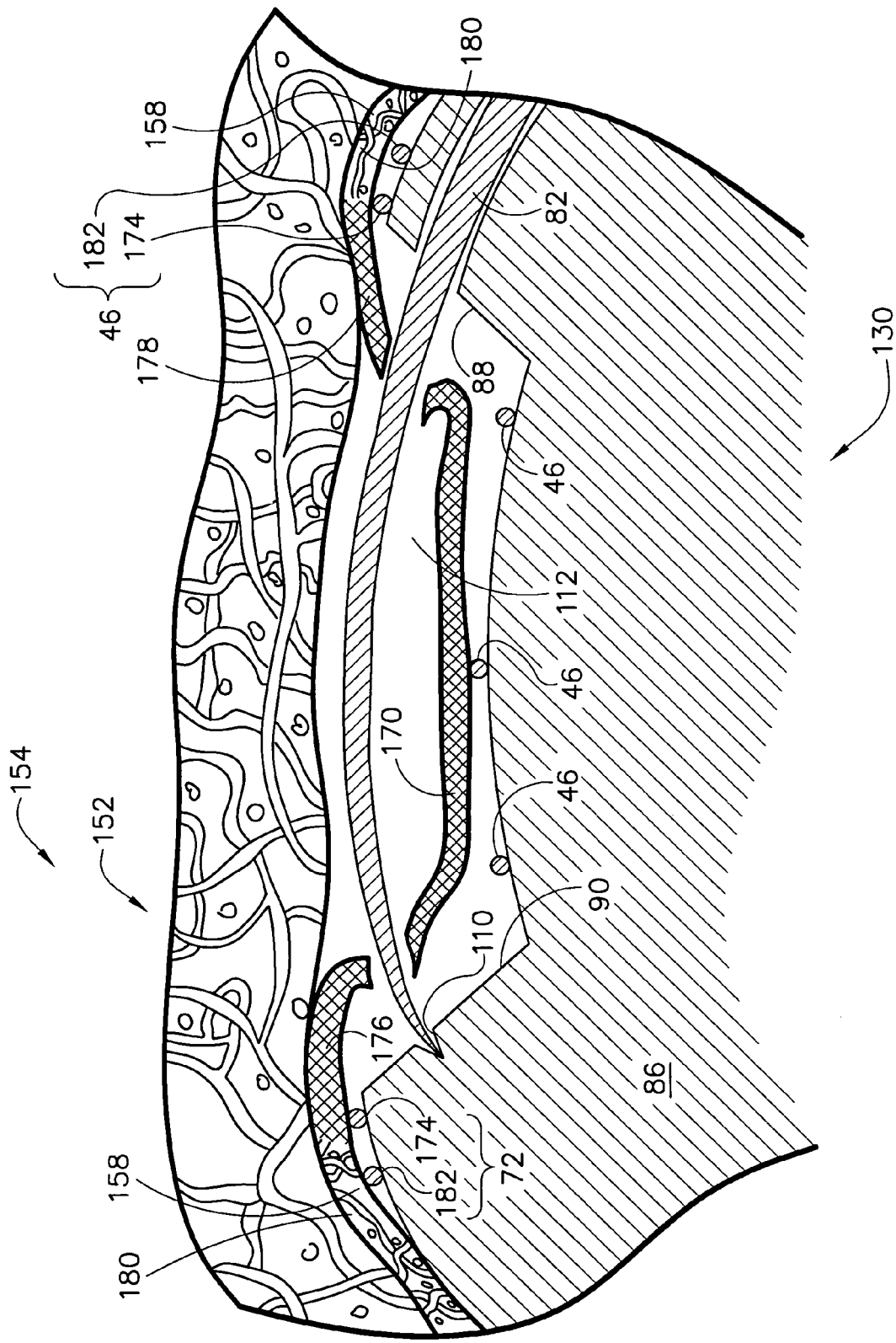

MUCOSAL ABLATION DEVICE

FIELD OF INVENTION

The present invention relates to a medical device, and more particularly to an ablation device for ablating tissue from a patient.

BACKGROUND OF THE INVENTION

Various devices and methods have been traditionally used to combat a physical condition known as Barrett's esophagus. Barrett's esophagus is the abnormal growth of intestinal type cells into the esophagus as a result of stomach acid chronically refluxing into the esophagus. Most people occasionally experience heartburn, which is the refluxing of stomach acid beyond the lower esophageal sphincter muscle and into the esophagus, and is not harmful. Severe or frequent reflux, however, is harmful and known by the names gastroesophageal reflux disease (GERD) and chronic reflux esophagitis (also known as Chronic Acid Reflux, or CAR). About one out of every ten patients with GERD/CAR are found to have a condition known as Barrett's esophagus. In patients with Barrett's esophagus, the healthy mucosal cells of the inner layer, or the squamous epithelium, of the esophagus are replaced with diseased, or intestinal cells. It is believed that such growth is a defense mechanism of the body to avoid esophageal injury due to the acid refluxed from the stomach. Unfortunately, these mucosal tissue changes may lead to low, then high grade dysplasia, and eventually to cancer of the lower esophagus, known as adenocarcinoma.

A common method for destroying diseased esophageal tissue has been to cauterize the unwanted tissue with a conventional ablation device. Ablation devices have developed as an alternative to other traditional means for eliminating unwanted tissue, such as by cutting away the tissue, cryotherapy, and thermal therapy. Cryotherapy is the application of extreme cold to freeze and destroy diseased mucosal tissue. Thermal therapy is the application of heat to burn diseased mucosal tissue. In use, these devices are placed next to or in contact with the unwanted tissue and tissue is ablated, cauterized, coagulated, frozen, or burnt, as the case may be, by energy transmitted from or to the device.

Traditional ablation devices have two primary shortcomings. First, traditional devices ablate only relatively small portions of patient tissue at one time. The energy transmitting elements of these conventional devices usually cover a portion of the outer surface of the device. Thus, the area ablated in a single energy transmission is substantially equal to the surface area covered by the energy transmitting elements. The area ablated in a single energy transmission with conventional devices is generally limited to a width of about 3 millimeters and a length of between 5 millimeters and 15 millimeters.

A second primary shortcoming of traditional ablation devices is their inaccuracy in use. A main challenge for battling Barrett's esophagus is to destroy targeted tissue without affecting healthy adjacent esophageal cells or muscular cells underlying the diseased tissue. Injury to the healthy underlying muscular tissue, for example, can lead to the creation of a stricture or constriction in the esophagus. Many conventional ablation devices have opaque probes for ablating tissue. The probes contain the energy transferring elements with which the unwanted tissue is destroyed. The inability to view through the probe leads to maneuvering difficulties and reduced accuracy in use. For instance, because the probe is not visually transparent, a user must estimate the position of the energy transferring elements when positioning of the device within the patient and during the energy transmitting procedure. The requirement to estimate the position of the elements during the energy transmission prevents the user from knowing whether the energy transmission has affected the targeted tissue until the tissue visible around the opaque tip has been affected. The likelihood of destroying healthy cells is greatly increased when such delayed and indirect feedback is used. Even with conventional devices having visually transparent probes, the accuracy is reduced by the inability to accurately identify and isolate the tissue to be ablated. For example, when electrodes on a conventional device are placed adjacent diseased tissue, there are no visual indicators accurately ensuring the device has been properly positioned and there are not safeguards to ensure healthy tissue next to the diseased tissue and underlying muscular tissue will not be adversely affected. The inability to accurately identify and isolate the tissue to be ablated can result in insufficient ablation. Thus, even when the probe is properly positioned, when too much energy is transferred to or from the device, ablation of healthy adjacent cells and/or underlying muscular cells can occur. On the other hand, when too little energy is transferred from the device, less than all of the targeted tissue is ablated.

The conventional approaches for treating Barrett's esophagus or other diseases requiring the precise ablation of relatively large areas of intralumenal tissue are insufficient in these regards. Thus, there is a need for an ablation device and method for using such a device that allow accurate and minimally invasive ablation of relatively large amounts of intralumenal patient tissue.

BRIEF SUMMARY OF THE INVENTION

The present invention relates to a medical device for performing a therapeutic procedure on a patient, and more particularly to an ablation device for ablating tissue in a patient. The device includes a body that is sized and shaped to engage a working end of an endoscope. The body has a recess therein. The device also includes an electrode positioned on the body and communicative with an energy source for delivering energy to the electrode when performing the therapeutic procedure on the patient. The device further includes an injection needle positioned in the recess and communicative with a fluid source for delivering fluid to the needle when performing the therapeutic procedure on the patient.

In another aspect, the present invention includes a method for performing a therapeutic procedure on a patient. The method includes positioning a device body having a recess therein to a desired location within the patient. The method also includes contacting the patient with the device body such that a portion of patient tissue becomes disposed within the recess of the device body and at least a tip of an injection needle connected to the device body is embedded below a surface of the patient tissue. The method further includes injecting fluid through the needle to a region below the tissue surface. Yet further, the method includes ablating the portion of patient tissue disposed in the recess by applying energy to the tissue portion through at least one electrode connected to the device body adjacent the recess.

Other aspects of the present invention will be in part apparent and in part pointed out hereinafter.

BRIEF DESCRIPTION OF THE FIGURES

FIG. 18 is the cross section of FIG. 17 shown after ablation of the cut tissue.

Corresponding reference characters indicate corresponding parts throughout the several views of the drawings.

DETAILED DESCRIPTION OF THE INVENTION

Figure 1:
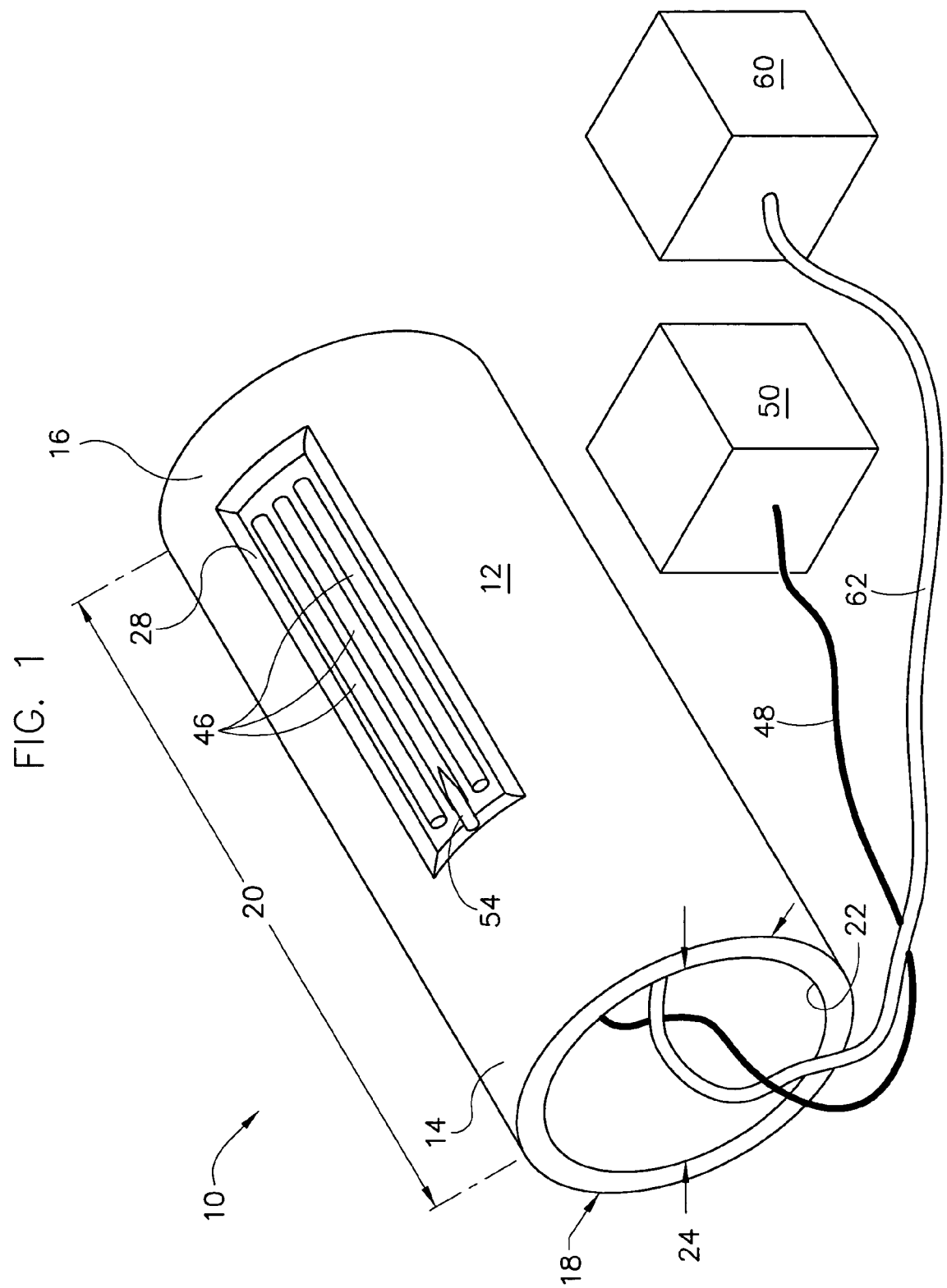
FIG. 1 is a perspective of a first embodiment of a medical device according to the present invention.
Figure 2:
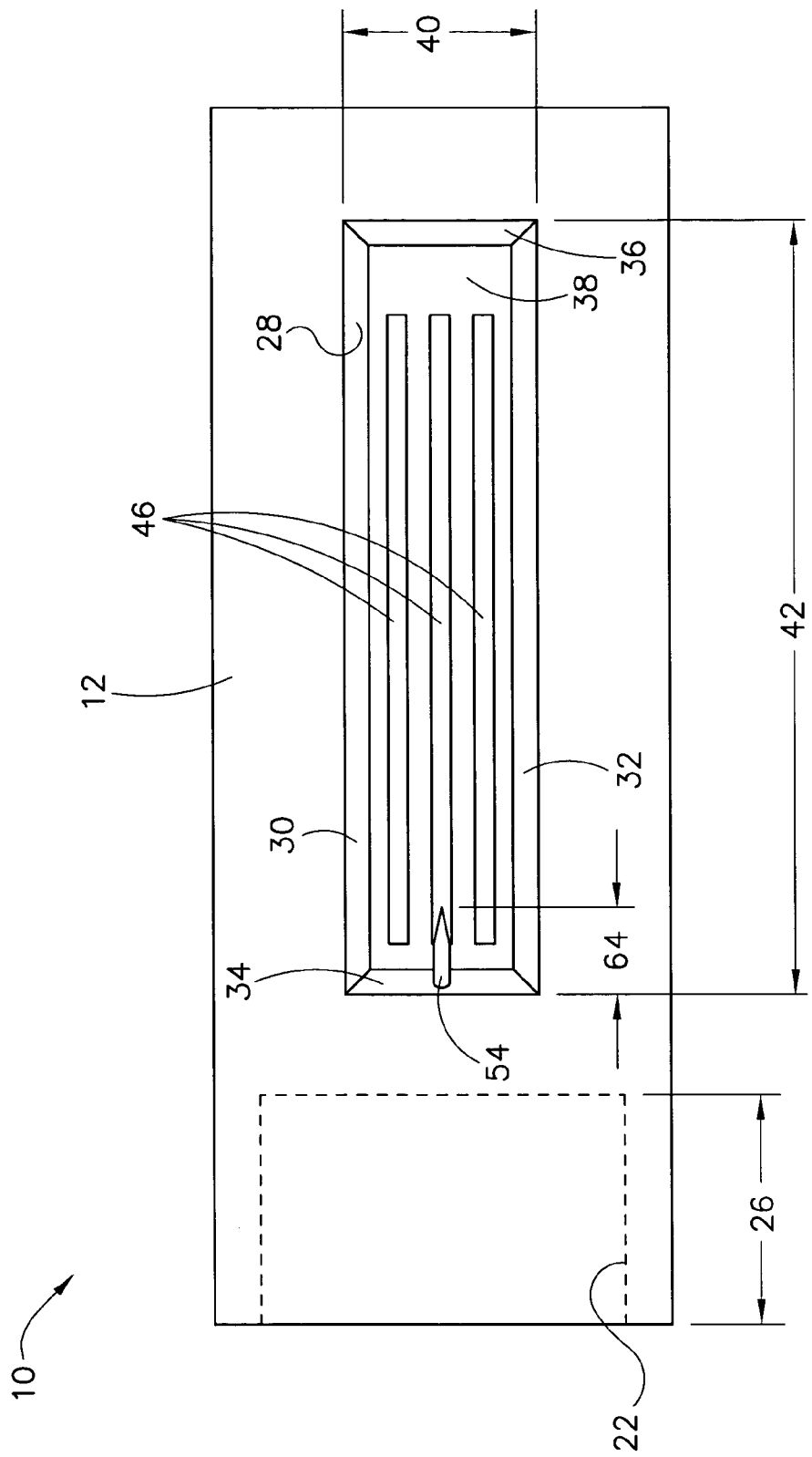
FIG. 2 is a top plan of the embodiment of the medical device shown in FIG. 1.

The present invention relates to a medical device for performing a therapeutic procedure on a patient, and more particularly for ablating unwanted tissue from a patient. Referring now to the figures, and more particularly to FIG. 1, a medical device according to a first embodiment of the present invention is designated in its entirety by reference number 10. The medical device 10 has an elongate body 12 extending from a source end 14 to a leading end 16. Although the body 12 may be made of other materials without departing from the scope of the present invention, in one embodiment the body is made of a visually transparent material, such as polycarbonate. Also, although the body 12 may have other shapes and dimensions without departing from the scope of the present invention, in one embodiment the body 12 is generally tubular and has an outer diameter 18 of between about 10 millimeters and about 20 millimeters and a length 20 of between about 25 millimeters and about 50 millimeters. The source end 14 of the body 12 is sized and shaped to engage a working end of an endoscope (not shown in FIGS. 1-9). In one embodiment, the source end 14 includes a circular receptacle 22 for receiving the working end of the endoscope. Although the receptacle 22 may have other diameters without departing from the scope of the present invention, in one embodiment the receptacle has a diameter 24 of between about 8 millimeters and about 15 millimeters. Also, although the receptacle 22 may have other depths without departing from the scope of the present invention, in one embodiment the receptacle 22 has a depth 26 of between about 2 millimeters and about 5 millimeters, as shown in FIG. 2.

Figure 3:
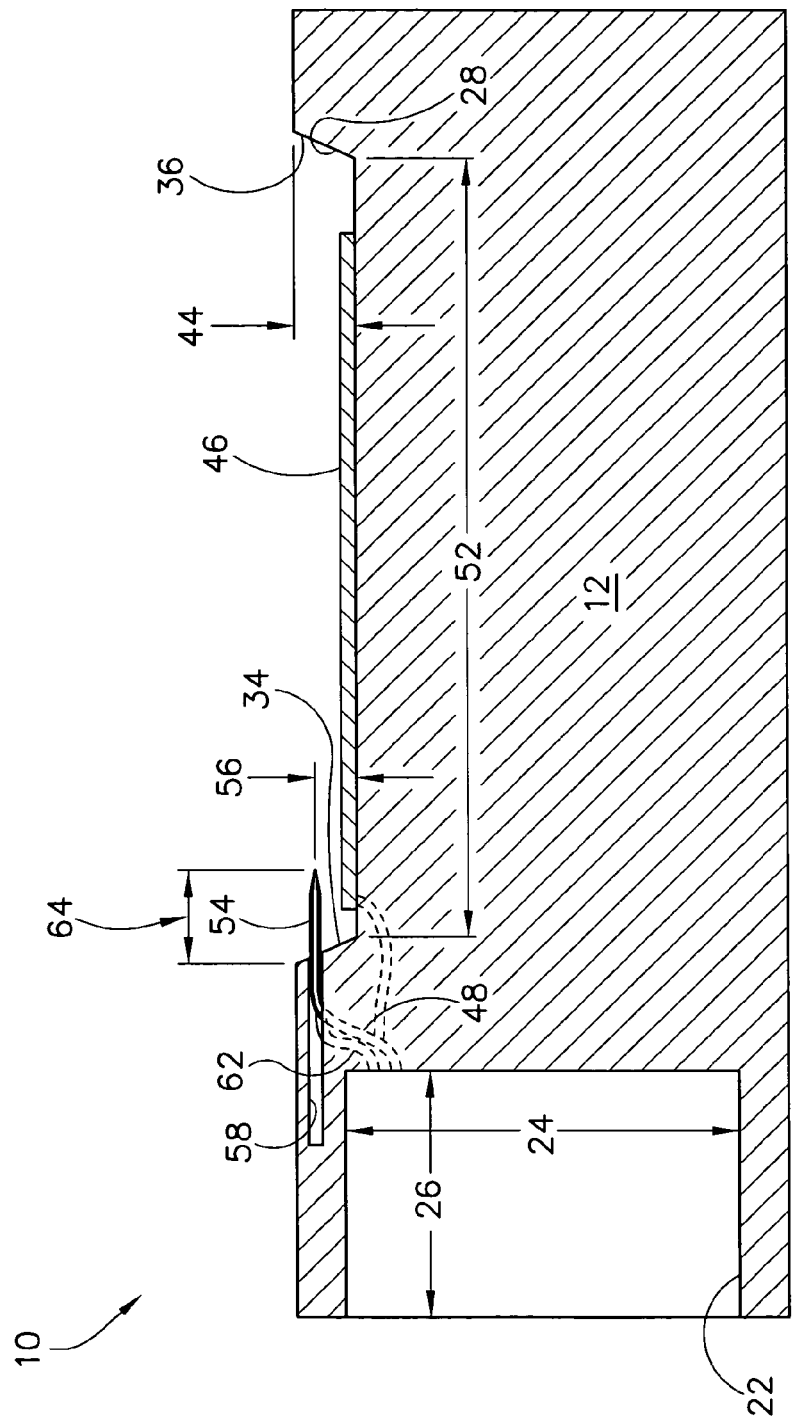
FIG. 3 is a side cross section of the embodiment of the medical device shown in FIG. 1.

The body 12 also comprises a recess 28 for receiving tissue to be ablated. In one embodiment, the recess 28 is elongate and rectangular having opposite sides 30, 32, opposite ends 34, 36 and a bottom 38. Although the recess 28 may have other dimensions without departing from the scope of the present invention, in one embodiment the recess has a maximum width 40 of between about four millimeters and about six millimeters and a length 42 of between about 18 millimeters and about 25 millimeters. Benefits of having an elongate recess 28 include the ability to accurately cover target tissue (not shown in FIGS. 1-10) with the device 10 because GERD/CAR tissue tends to be shaped as elongate fingers due to the splashing of stomach acid above the sphincter. Although the recess 28 may have other depths without departing from the scope of the present invention, in one embodiment the recess 28 has a depth 44 of between about 1 millimeter and about 2 millimeters, as shown in FIG. 3.

The device 10 further includes at least one recess electrode 46 connected to the body 12. A wire 48 connects the recess electrodes 46 to an energy source 50 for delivering energy to the recess electrode when performing a procedure on a patient (not shown). Although other energy sources may be used without departing from the scope of the present invention, in one embodiment the energy source 50 is an electrical generator for delivering electrical current to the electrodes 46. Although such an electrical generator may produce electrical current having other characteristics without departing from the scope of the present invention, in one embodiment the current produced has a power of between about 20 watts and about 30 watts, has a current of about 0.5 amps, has a voltage of between about 20 volts and about 500 volts, and has a frequency of between about 0.3 megahertz and about 1.0 megahertz. In another embodiment, the energy source 50 is a radio frequency generator for delivering radio frequency energy to the recess electrodes 46. Although such a radio frequency generator may produce signals having other characteristics without departing from the scope of the present invention, in one embodiment the radio frequency generator produces a signal having an amplitude of between about 20 volts and about 500 volts and a frequency of between about 0.3 megahertz and about 1.0 megahertz. In yet another embodiment, the energy source 50 delivers ultrasonic energy to the recess electrodes 46. Although such an ultrasonic generator may produce signals having other characteristics without departing from the scope of the present invention, in one embodiment the ultrasonic generator produces a signal having a frequency of between about 10 kilohertz to about 100 kilohertz. Although the number of recess electrodes 46 may vary without departing from the scope of the present invention, in one embodiment there are three electrodes 46. Although the positions of the recess electrodes 46 may vary without departing from the scope of the present invention, in one embodiment the recess electrodes 46 extend along the body 12 within the recess 28 separated from each other by a distance of between about 0.5 millimeters and about 2 millimeters. In one embodiment of the present invention, there are no electrodes outside of the recess. Although such recess electrodes 46 may be made of other materials without departing from the scope of the present invention, in one embodiment the electrodes 46 are made of a 26 gage stainless steel wire. Further, although the recess electrodes 46 may have other lengths, in one embodiment the electrodes 46 have a length 52 of between about 5 millimeters and about 25 millimeters.

The device 10 further includes an injection needle 54 connected to the body 12 within the recess 28. Although the needle may be oriented in the recess 28 in other ways without departing from the scope of the present invention, in one embodiment the needle 54 is circumferentially centered between the sides 30, 32, within the recess 28 and spaced from the recess bottom 38 by a distance 56 of between about 0.5 millimeters and about 1 millimeter and spaced from the top of the recess by a distance of between about 0.5 millimeters and about 1 millimeters. Although the needle 54 may be connected to the body 12 in other ways without departing from the scope of the present invention, in one embodiment the needle 54 is slidably disposed within a slot 58 in the body 12. The injection needle 54 is communicative with a fluid source 60 by way of a tube 62 for delivering fluid to the needle during the procedure. The fluid source 60 delivers an electrically conductive fluid to the needle 54 during the procedure. Although other fluid sources may be used without departing from the scope of the present invention, in one embodiment the fluid source 60 is a conventional saline source for delivering saline to the needle 54. The injection needle 54 is also communicative with the energy source 50 by way of the wire 48 for delivering energy to the injection needle when performing the procedure on the patient (not shown in FIGS. 1-11). Although the needle 54 may be made of other materials without departing from the scope of the present invention, in one embodiment the needle is made of a 23 gage stainless steel. Although the needle 54 may have other lengths without departing from the scope of the present invention, in one embodiment the needle, when deployed into the recess 28, has an exposed length 64 of between about 10 millimeters and about 20 millimeters. Also, although the needle may be spaced from the second end of the recess by other distances, in one embodiment the tip of the needle 54 is spaced from the second end 36 of the recess 28 by a distance of between about 10 millimeters and 20 millimeters.

Figure 4:
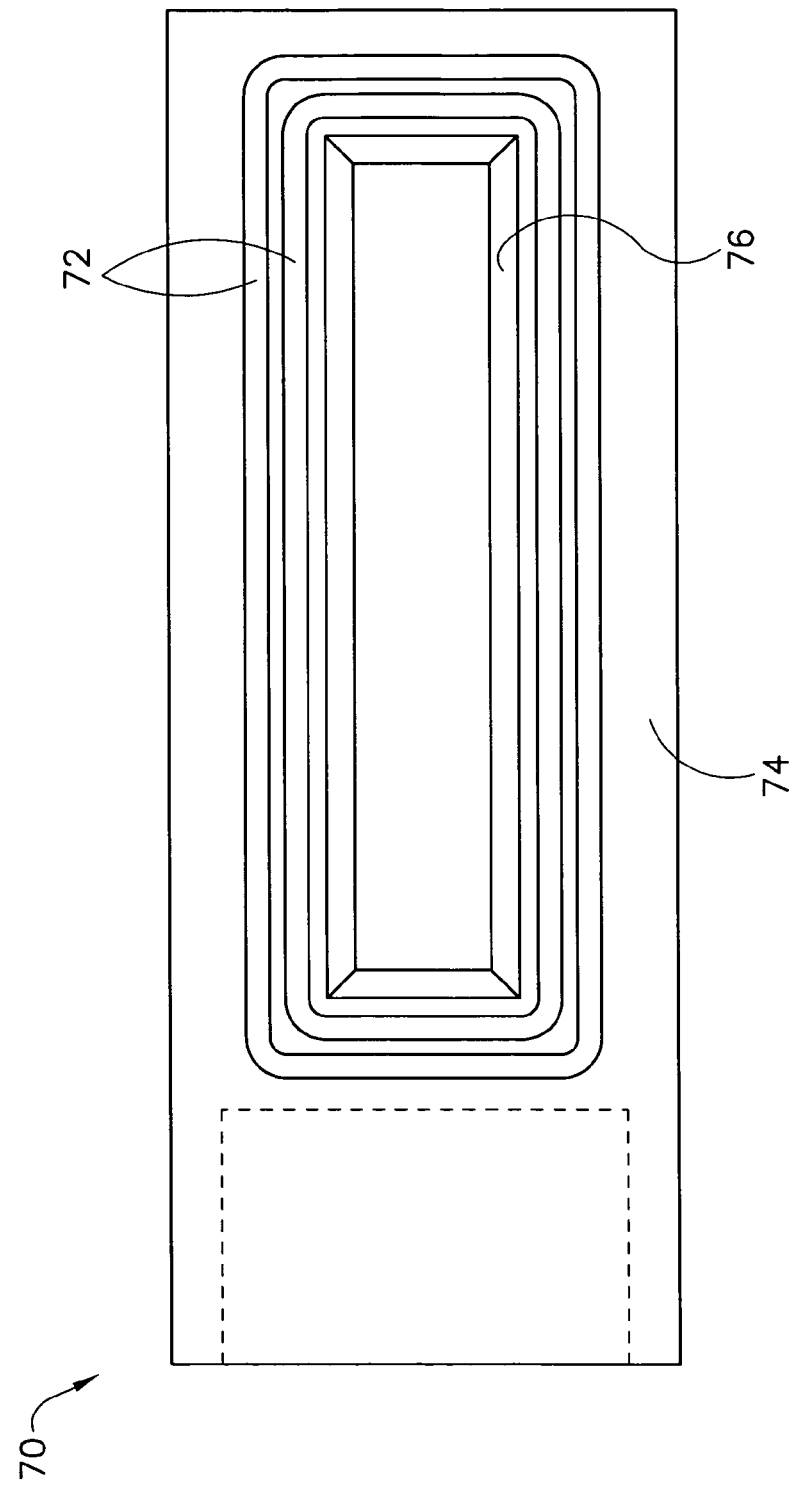
FIG. 4 is a top plan of a second embodiment of a medical device according to the present invention.
Figure 5:
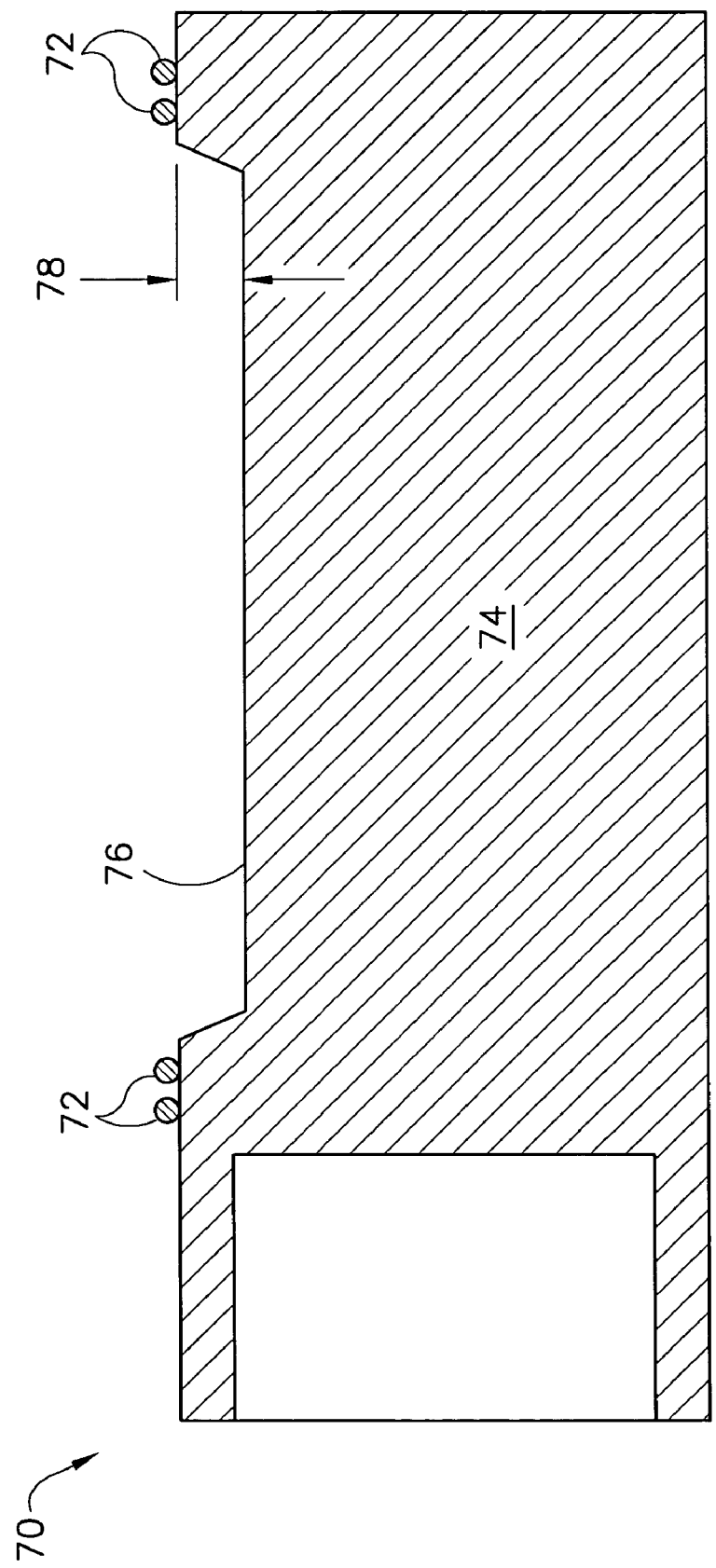
FIG. 5 is a side cross section of the embodiment of the medical device shown in FIG. 4.

FIG. 4 shows a second embodiment of a medical device 70 according to the present invention having at least one surface electrode 72 disposed on the body 74 outside of the recess 76. Hereinafter, reference number 72 will be used to reference a single or multiple surface electrodes, as the case may be. FIGS. 4 and 5 show two surface electrodes 72 disposed around the recess 76. Although the recess 76 of this embodiment may have other depths 78 without departing from the scope of the present invention, in one embodiment, the depth 78 is between about 0.5 millimeters and about 2 millimeters. The electrodes 72 of this embodiment are otherwise identical to the electrodes of the earlier described embodiments, and therefore will not be described in further detail.

In one embodiment, adjacent electrodes carry varying charges when the medical device is in use. For example, with either the radio frequency or the electrical power generators 50, the two adjacent surface electrodes 72 shown in FIGS. 4 and 5 can have opposite polarities. Similarly, adjacent recess electrodes 36 shown in FIGS. 1 and 2 can have opposite polarities such that the recess electrode in the center has a charge that is opposite of the charge of the outer recess electrodes. For instance, the outer recess electrodes can carry a positive charge while the central recess electrode carries a negative charge. Also, the needle 54 may have a polarity that differs from the electrodes 36, 72. For example, when adjacent recess electrodes 46 carry opposite charges, the needle 54 may carry the same charge as the outer recess electrodes. Such bipolar energy transmission is generally safer than mono-polar energy applications which tends to create coagulation zones that are too deep. Also, the characteristics of each electrode 46, 72, when such characteristics differ as described, may change. That is, the characteristics of the electrodes 46, 72 and needle 54 may alternate or otherwise change with time during use of the medical device 10, 70. Such varying signal characteristics, or multiplexing, results in higher levels of energy concentrated at and delivered from the electrodes 46, 72 and needle 54 as a result of the interaction between the differing signals between the adjacent electrodes and the needle.

Figure 6:
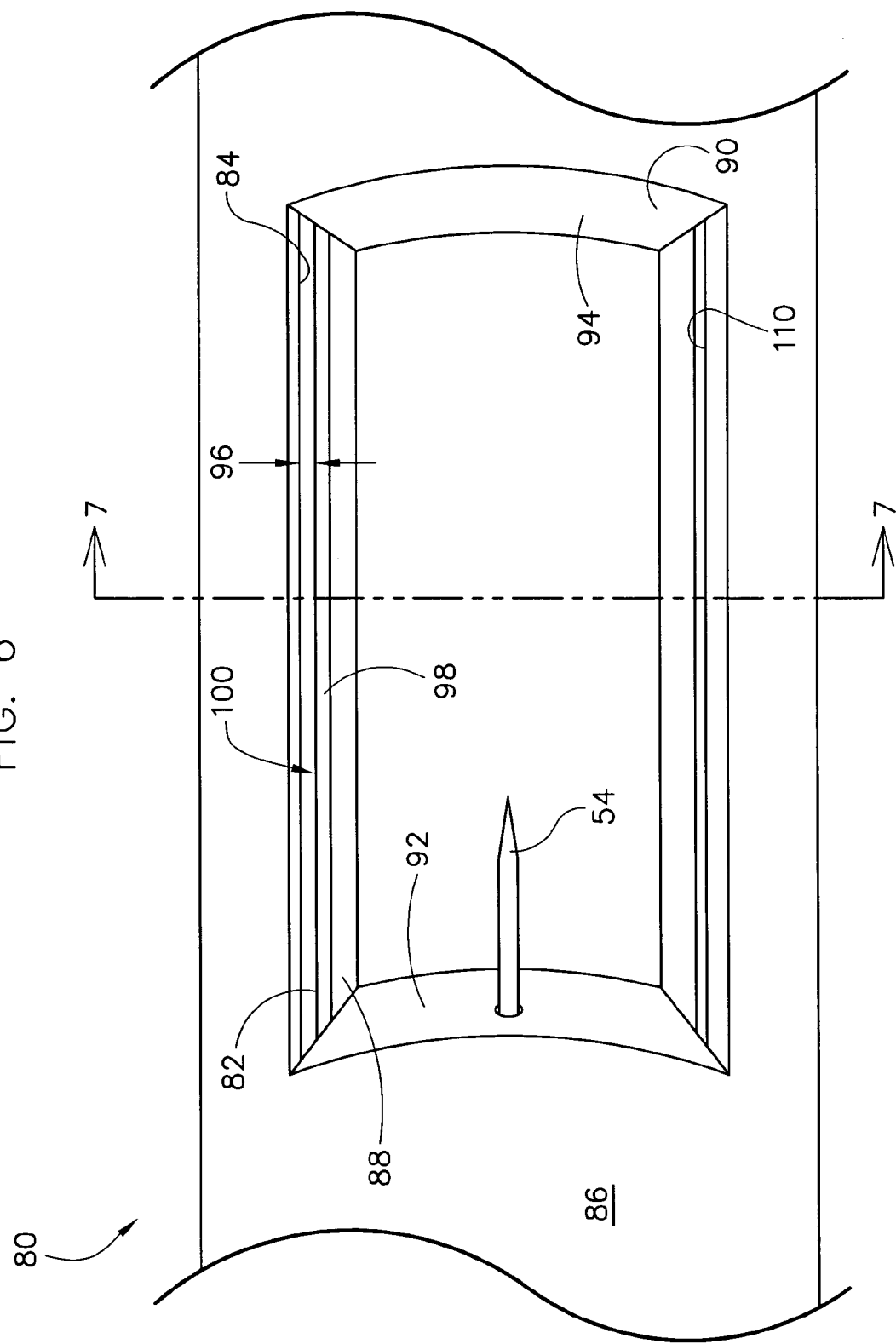
FIG. 6 is a detail top plan of a third embodiment of a medical device according to the present invention
Figure 7:
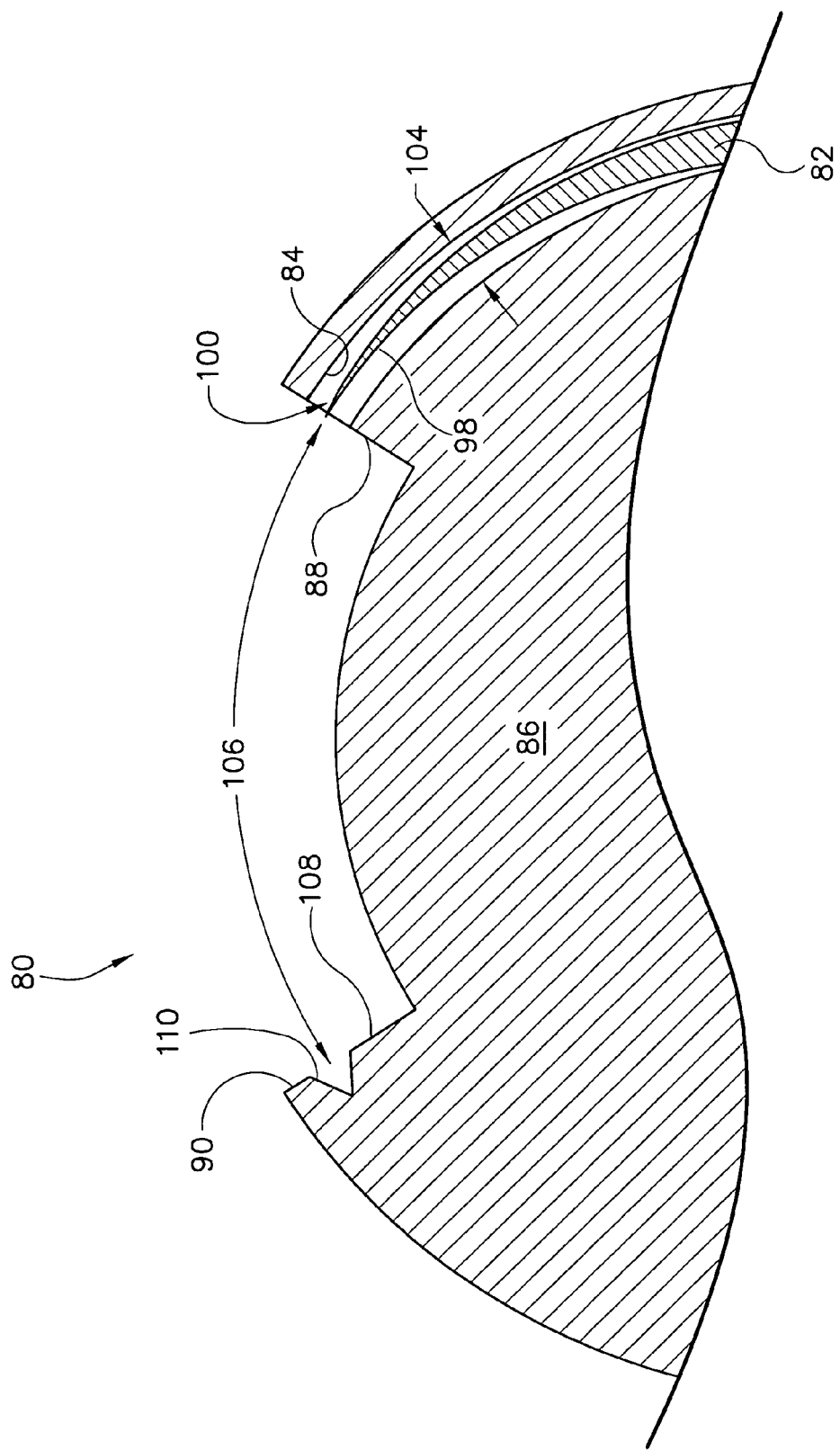
FIG. 7 is a cross section of the third embodiment of the medical device taken along line 7-7 of FIG. 6.
Figure 8:
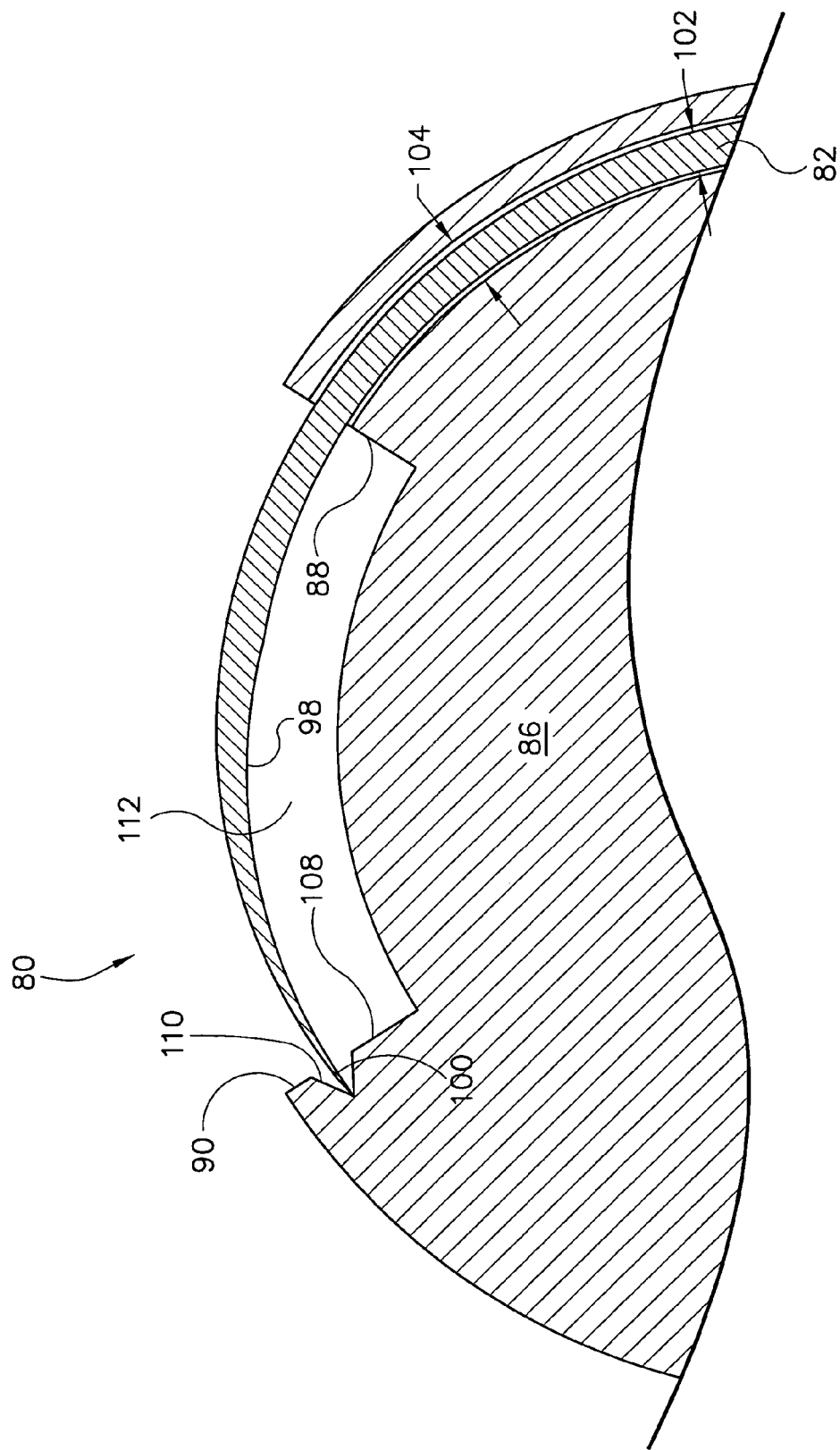
FIG. 8 is the cross section of FIG. 6 shown with a deployed blade.

FIG. 6 shows a third embodiment of a medical device 80 according to the present invention having a blade 82 slidably disposed in a blade recess 84 of the device body 86. Although the blade recess may be located in other locations without departing from the scope of the present invention, in one embodiment of the present invention the blade recess 84 is located in one side 88 of the recess 90. As an alternate example, the blade 82 may extend out of either end 92, 94 without departing from the scope of the present invention. Although the blade recess 84 may have other dimensions without departing from the scope of the present invention, in one embodiment, the blade recess 84 has an opening thickness 96 of between about 0.5 millimeters and 2 millimeters. Also, although the blade may be made of other materials without departing from the scope of the present invention, in one embodiment the blade 82 is made of stainless steel. The blade 82 is attached to an actuator (not shown) for moving the blade 82 into the recess 90 when performing the therapeutic procedure. Example actuators include springs, hydraulic sources, pneumatic sources, magnetics, and electric motors. As a specific example of an actuator, an electric motor (not shown) may be connected to a high friction roller (not shown) contacting the underside 98 of the blade 82 for moving the blade into the recess 90. Although the blade 82 may have other dimensions without departing from the scope of the present invention, in one embodiment the blade 82 tapers from a sharp tip 100 at one end to a base having a thickness 102 slightly less than the blade recess thickness 104. The blade 82 has a width that is greater than the circumferential distance 106 between the sides 88, 108 of the recess 90. FIGS. 6 and 7 show the third embodiment of the medical device 80 in which the blade 82 is retracted into the recess 84. FIG. 8 shows this embodiment of the medical device 80 when the blade 82 is in a deployed state wherein the blade extends into the recess 90. As shown in FIGS. 7 and 8, the device body 86 may include a blade receiving notch 110. The notch 110 receives the blade tip 100 to allow more efficient cutting of the patient tissue (not shown in FIGS. 1-11) when the blade 82 is deployed. After deployment of the blade 82, patient tissue is trapped in the compartment 112 formed by the recess 90 and the blade 82.

Figure 9:
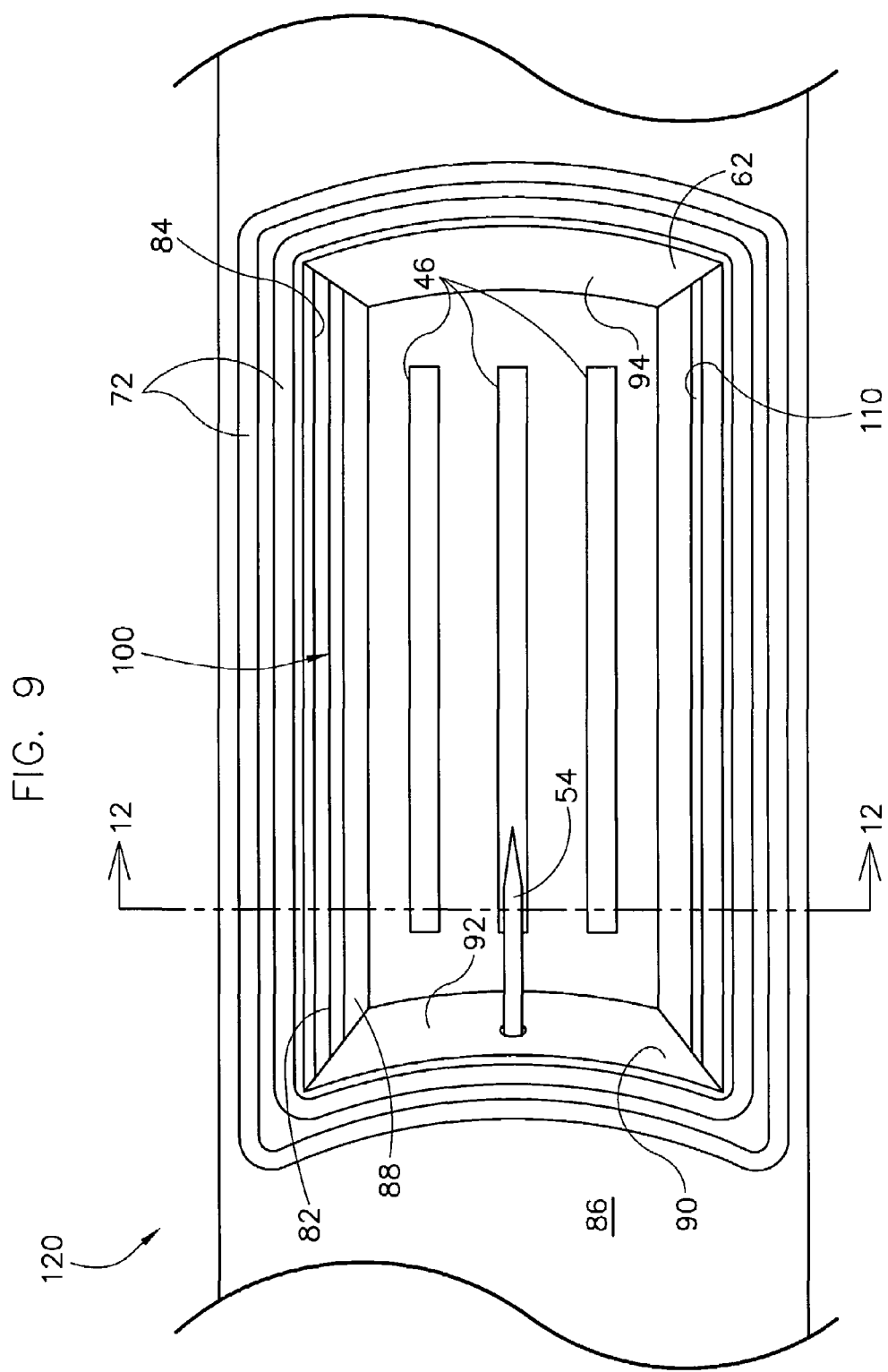
FIG. 9 is a detail top plan of a fourth embodiment of a medical device according to the present invention.

Although the device 80 having the blade 82 is shown in FIGS. 6-8 without electrodes and needles, any of the foregoing electrode or needle configurations can be included with the embodiments of the device 80 having the blade 82 without departing from the scope of the present invention. For example, FIG. 9 shows a device 120 having three recess electrodes 46 and two surface electrodes 72. Further, although not shown in FIGS. 6-8, the device 120 may include a needle 54 at one end 92 of the recess 90 within or outside of the trajectory of the blade 82 without departing from the scope of the present invention. That is, a needle may be disposed radially inside or outside the compartment 112 when the blade is in the deployed position shown in FIG. 8. For example, FIG. 9 shows a device 120 having a needle 54 disposed at one end 92 within the trajectory of the blade, and thus within the compartment 112 formed by the blade 82 and the recess 90. The electrodes and needles of these embodiments are otherwise identical to the electrodes of the earlier described embodiments, and therefore will not be described in further detail.

In an embodiment of a medical device 120 according to the present invention having at least one electrode 46 or 72, the blade 82 also communicates with the power source 50 by way of wire 48 for delivering energy to the blade 82 during the therapeutic procedure. In another embodiment, the needle 54, blade 82, and one or more electrodes 46, 72 are simultaneously communicative with the power source 50. Also, the charge on adjacent elements may differ. Such bipolar energy transmission is beneficial as described above regarding earlier embodiments. Multiplexing, or varying of signal characteristics with time, may also be implemented with these embodiments where the blade 82 is communicative with the energy source 50. Such multiplexing is beneficial as described above regarding earlier embodiments.

Figure 10:
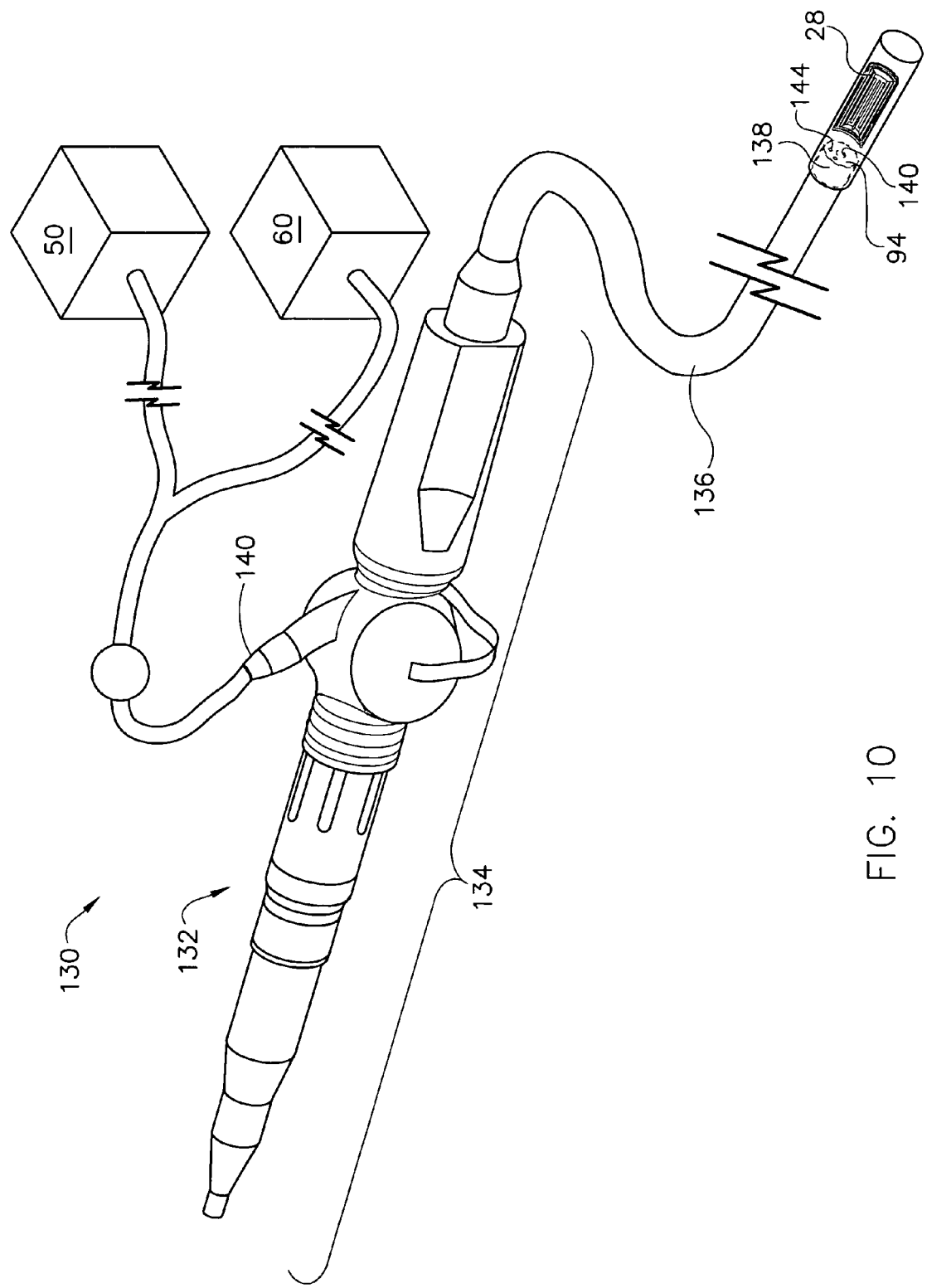
FIG. 10 is a perspective of the device in combination with a conventional endoscope.

FIG. 10 shows a fourth embodiment of a medical device 130 according to the present invention including an endoscope 132. Although FIG. 10 shows one type of endoscope 132, any conventional type of endoscope may be used without departing from the scope of the present invention. The endoscope 132 may be a flexible endoscope, such as those commonly used in upper gastrointestinal endoscopy examinations, or esophagogastroduodenoscopy (EGD). The endoscope 132 has an elongate primary body 134 and an elongate tubular portion 136 (e.g., flexible shaft) extending from the body 134 to a working end 138. The endoscope 132 also has a working channel 140 beginning at an entry port 142 on the primary body 134 and terminating at a terminal port 144 at the working end 138 of the shaft 136. The working channel 140 receives the wire 48, tube 62, or both for the embodiments having an endoscope and a wire and/or tube.

Figure 11:
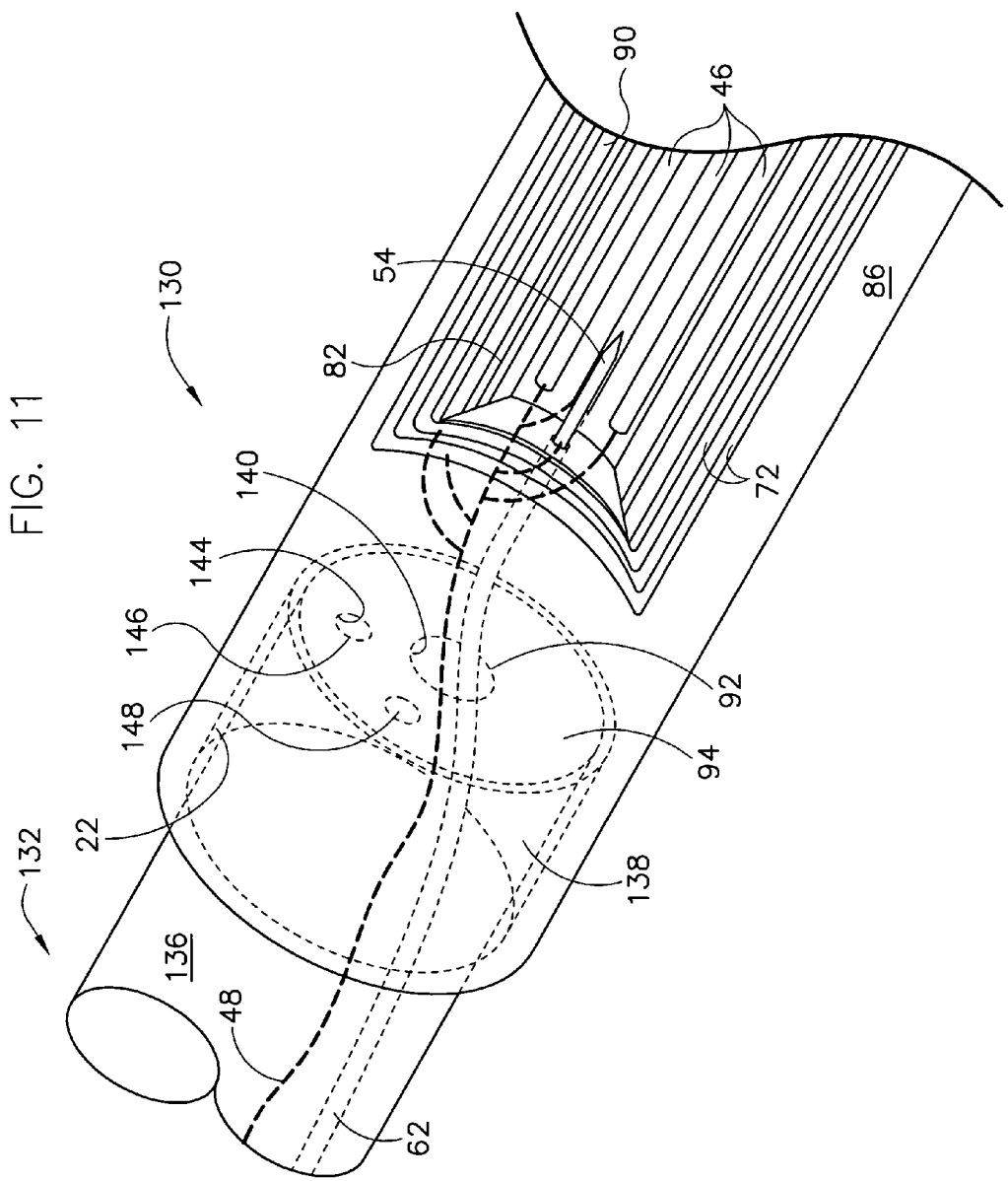
FIG. 11 is detail perspective of a portion of the combination shown in FIG. 10.

As shown in FIG. 11, the medical device 130 can have viewing optics 144 for viewing an object (not shown) positioned in a viewing area (not shown) adjacent the working end 138 of the endoscope 132. The viewing area includes all the objects visible through the viewing optics 144, including the recess 90 of the device body 86 and adjacent tissue (not shown in FIGS. 1-11). Although the viewing area may have other shapes without departing from the scope of the present invention, in one embodiment the area is circular. The optics 144 are disposed within the endoscope 132, beginning at a location (not shown) near the primary body 134, where a user may receive images, and terminating near an optics orifice 146. The endoscope 132 further has an illuminator 148 for directing light toward the recess 90 and an object (not shown) positioned adjacent the working end 138 of the shaft 136. As with the optics 144, the illuminator 148 originates at a location (not shown) near the primary body 134 and terminates near the working end 138. The device body 86, electrodes 46, 72, needle 54, and blade 82 of this embodiment are otherwise identical to those of the earlier described embodiments, and therefore will not be described in further detail.

A primary purpose for the ablation device is to ablate diseased esophageal tissue for combating Barrett's esophagus. Although the medical device is described as ablating abnormal esophageal mucosa in humans, the device may ablate other tissues, tissues in other animals, or things other than tissue without departing from the scope of the present invention.

In operation, a user of an ablation device 130 according to the present invention first inserts the working end 138 of the endoscope 132 into the receptacle 22 in the device as shown in FIG. 11. The needle 54, electrodes 46 and 72, and blade 82 are connected to the energy source 50 by way of wire 48. After positioning the device body 86 as described, the user moves the device body 86 to a desired location adjacent the area of desired ablation such as at a lower end of an esophagus of a patient (not shown in FIGS. 1-11). The desired location is adjacent diseased lumenal tissue. If desired, the user can verify that the body 86 and endoscope 132 are properly positioned by viewing at least one electrode 46 positioned in the recess 90 through the device body 86. The positioning may include articulating and/or translating the shaft 136 of the endoscope 132.

Figure 12:
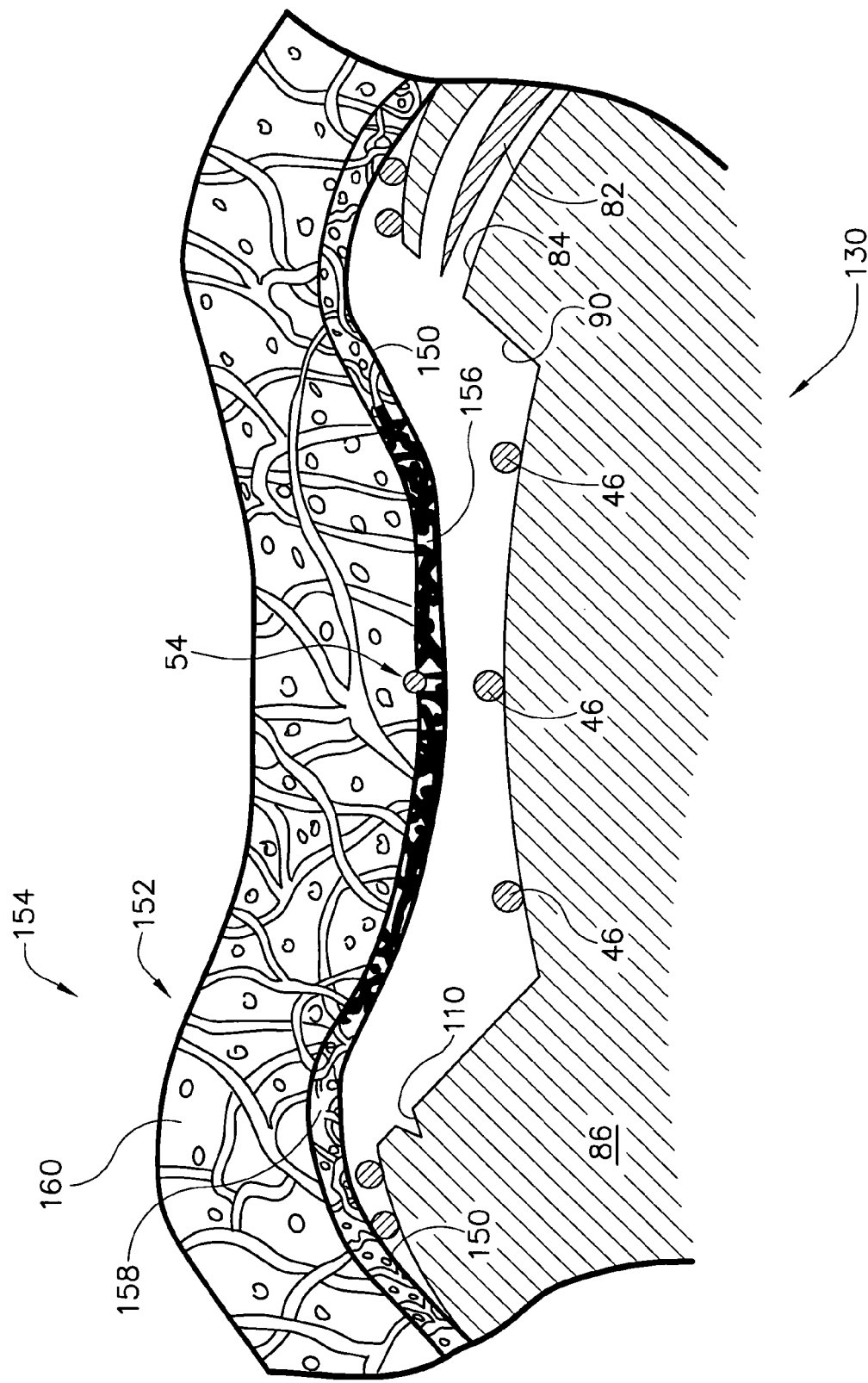
FIG. 12 is cross section of the fourth embodiment of the medical device taken along line 12-12 of FIG. 9 shown contacting tissue in a patient.
Figure 13:
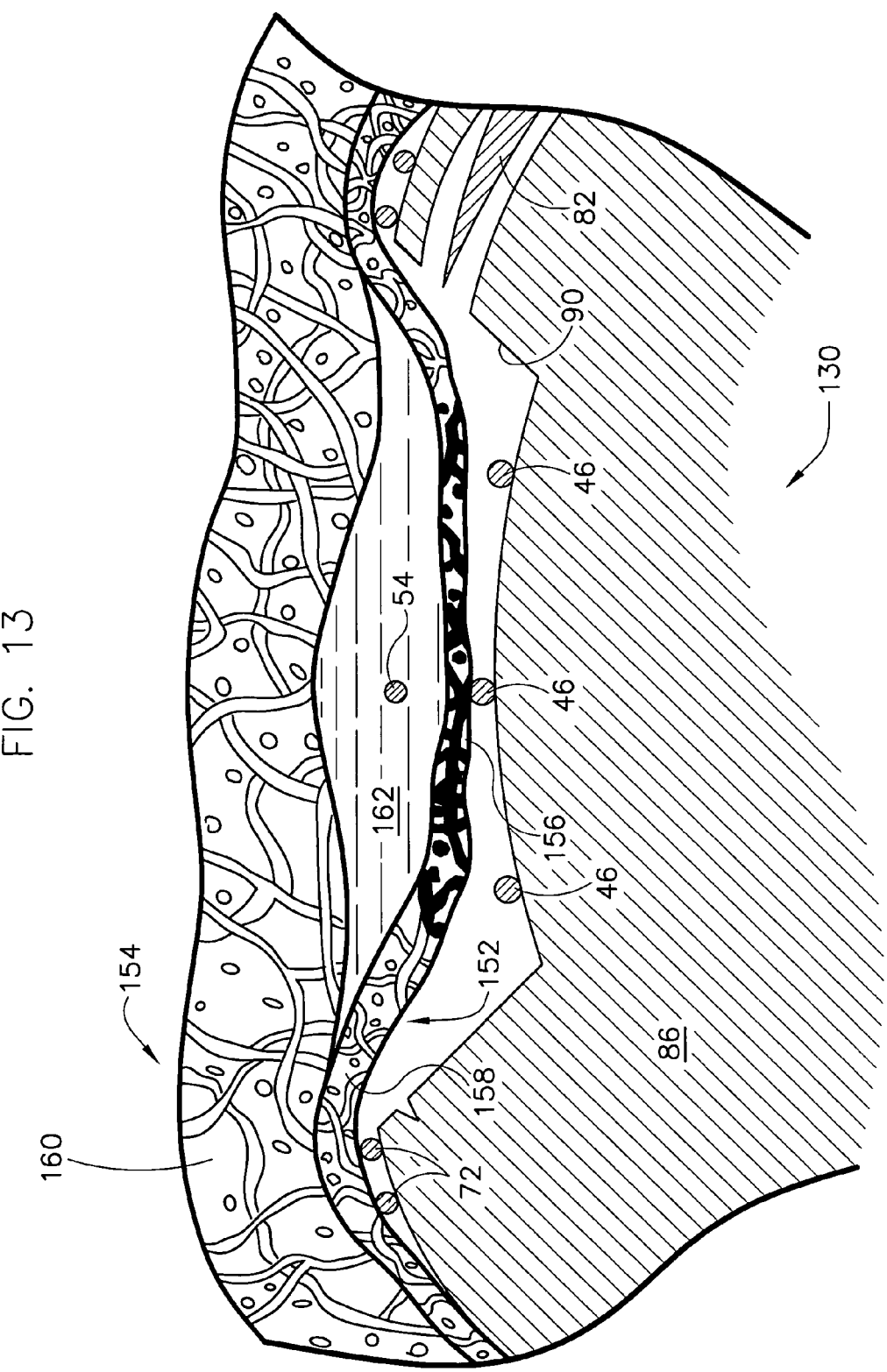
FIG. 13 is the cross section of FIG. 12 shown after fluid has been injected through the needle into the tissue.
Figure 14:
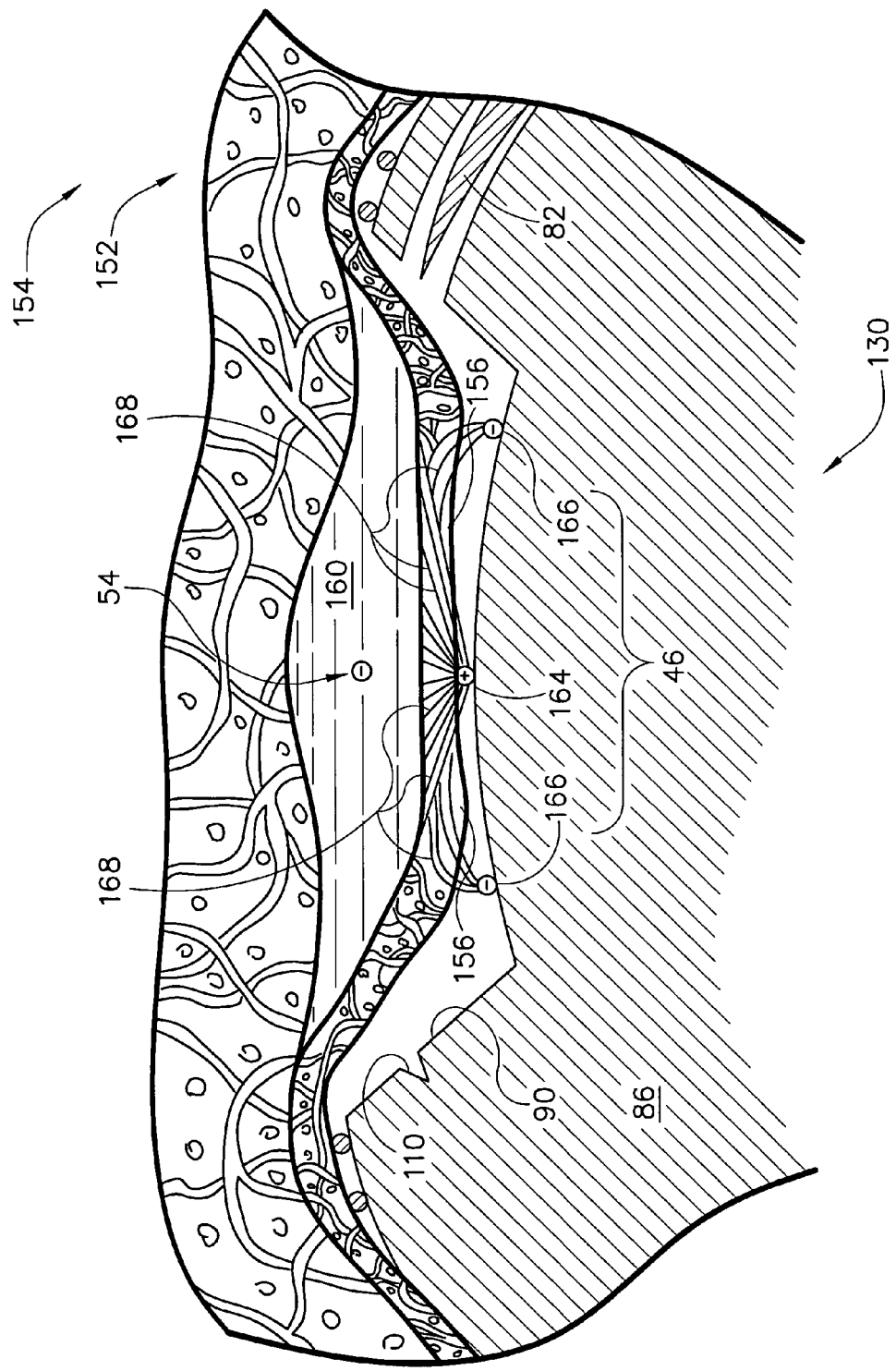
FIG. 14 is the cross section of FIG. 13 shown during ablation of target tissue.
Figure 15:
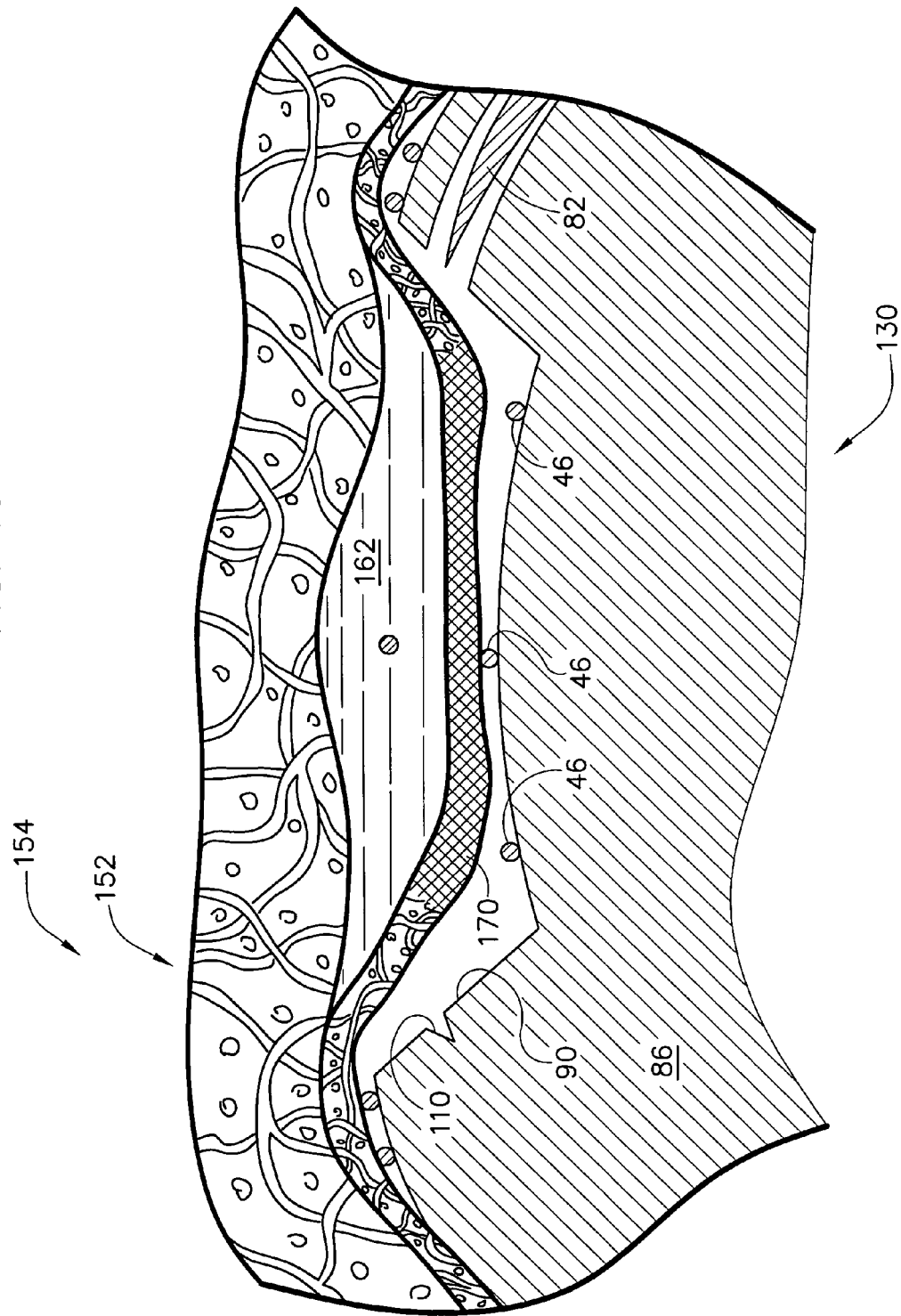
FIG. 15 is the cross section of FIG. 14 shown after ablation of the target tissue.

After the medical device 130 has been positioned as described, the user moves the device toward the tissue so the device body 86 near the recess 90 contacts the tissue (i.e., an inner wall 150 of a lumen 152 of a patient 154), as shown in FIG. 12. Contacting the lumen 152 near target tissue 156 with the portion of the device body 86 near the recess 90 causes the lumen 152 to become at least partially disposed within the recess 90. The user may then view the recess 90 and the lumen 152 to accurately ensure proper positioning of the device 130 with respect to the target tissue by seeing which tissue becomes disposed in the recess 90. As the lumen 152 becomes disposed within the recess 90, at least the tip of the needle 54 becomes embedded into the first, mucosal layer 158, but not beneath the second, muscularus layer 160 of tissue in the lumen 152. In this way, the needle 54 becomes disposed between the mucosal layer 158 and the muscularus 160 of the lumen 152. The user then injects fluid 162 into the tissue by way of the injection needle 54 thereby causing the mucosal layer 158 and the muscularus 160 to separate, as shown in FIG. 13. Once the fluid 162 has been injected between the mucosa 158 and muscularus 160, the user can then ablate the target tissue 156 by energizing the recess electrodes 46 and needle 54. In one embodiment, the recess electrodes 46 and needle 54 are energized for between about 1 second and about 2 seconds. For example, in one embodiment, the recess electrodes 46 and needle 54 was energized for 1.3 seconds. Adjacent recess electrodes 46 can carry opposite charges and the needle 54 can carry a charge that is opposite to the central electrode 164 of the recess electrodes 46. Specifically, as shown in FIG. 14, the central recess electrode 164 may carry a positive charge while the outer recess electrodes 166 carry negative charges. Alternatively, the central recess electrode 164 may carry a negative charge while the outer recess electrodes 166 and needle 54 carry positive charges. The varying charges (i.e., bipolar configuration) creates electrical signals 168 that transmit through and ablate the target tissue 154. FIG. 15 shows the ablated target tissue 170. If the user decides not to remove the ablated tissue 170 directly, as described below, the destroyed tissue 170 will be sloughed off (i.e., through the normal digestive process) within a short period of time after the procedure and healthy mucosal tissue will grow in its place.

Figure 16:
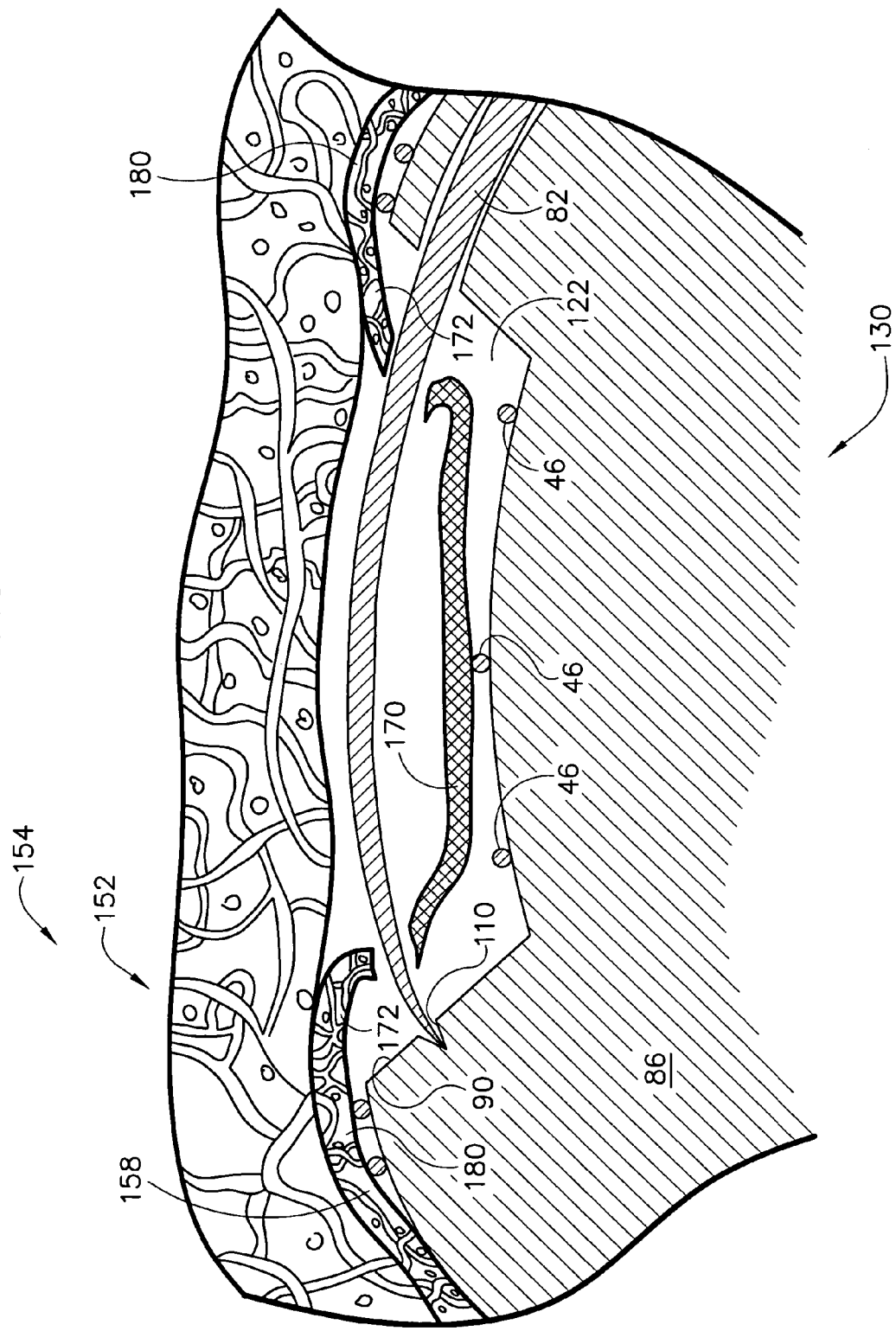
FIG. 16 is the cross section of FIG. 15 shown after the blade has been deployed.
Figure 17:
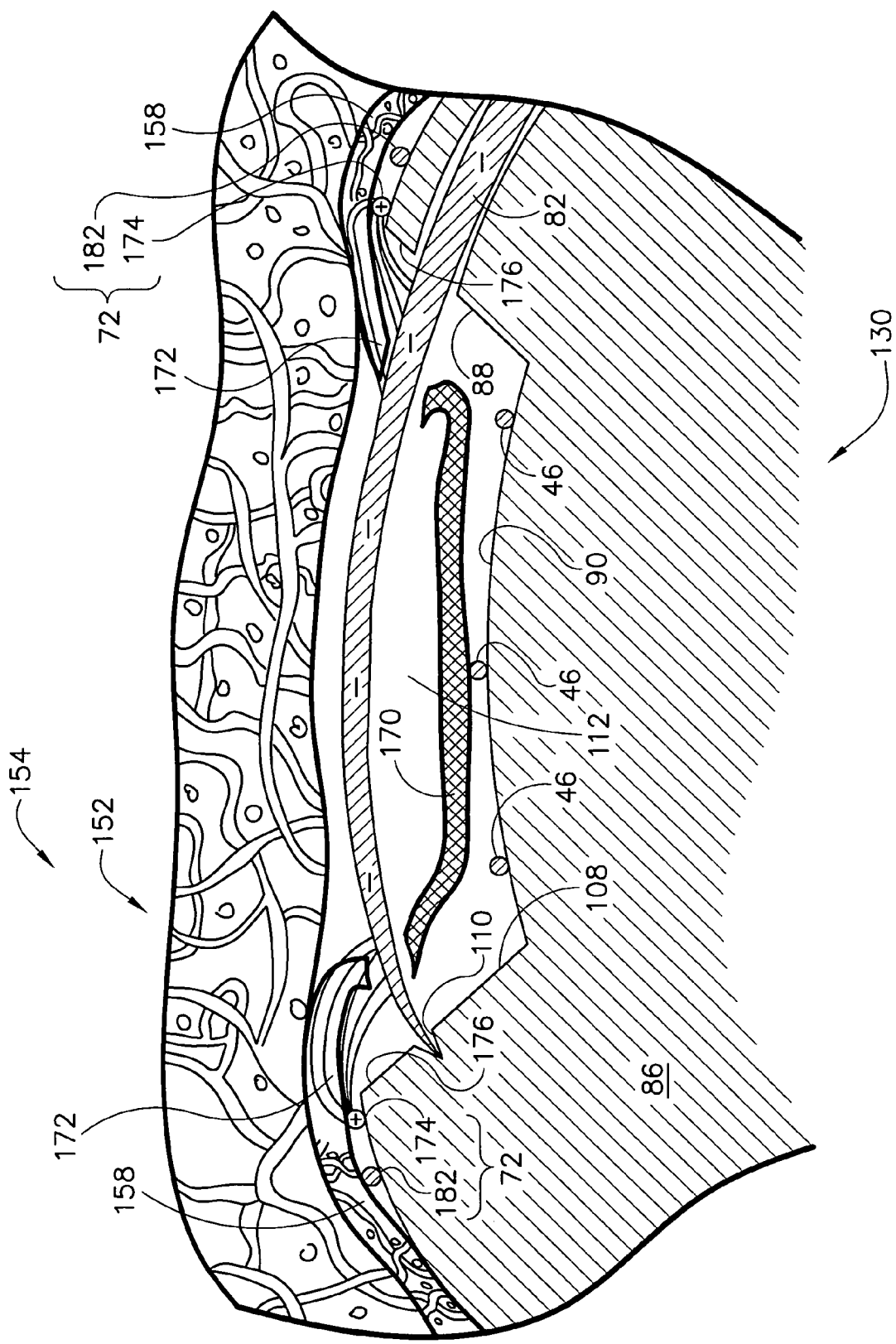
FIG. 17 is the cross section of FIG. 16 shown during ablation of cut tissue.

After ablating the target tissue 156, the user can resect (i.e., cut) the ablated tissue 170 from the patient 154 by deploying blade 82 from the stored position, shown in FIGS. 10-15, to a deployed position, shown in FIG. 16. In this way, the ablated tissue 168 becomes trapped in a cavity 112 formed by the recess 90 and the blade 82 and may be removed from the patient 154 for analysis. The user may also desire to coagulate or cauterize at least the ends 172 of the mucosa 158 remaining in the patient 154 after the resection of the ablated tissue 170. Specifically, the user may energize the surface electrodes 72 and the blade 82 with varying charges. For example, the inner surface electrode 174 of the two surface electrodes 72 may carry a positive charge while the blade 82 carries a negative charge, as shown in FIG. 17. In one embodiment (not shown), an electrode carrying a charge that is opposite to the charge of the blade 82 is located at locations 176 on the side walls 88, 108 of the recess 90 outside of the trajectory of the blade 82. FIG. 18 shows the coagulated/cauterized edges 178. The user may also desire to ablate portions 180 of the mucosa 158 adjacent the extreme ends 178 by energizing the outer surface electrode 182 of the two surface electrodes 72 while energizing the inner surface electrode 170 and/or the blade 82. Along with bipolar energy transmission, any of the energizing steps may include multiplexing as described regarding earlier embodiments of the present invention. Benefits of ablating tissue 172, 180 remaining in the patient after resection of the ablated tissue 170 include limiting bleeding, disinfection, and otherwise avoiding injury to the patient 154.

By this local and accurate ablation method, diseased mucosal tissue is destroyed. The type of energizing may be of any conventional type, including the types mentioned above regarding energy source 50, such as radio frequency, electrical, and ultrasonic. Although the procedure described was described with reference to medical device 130, it will be appreciated by those skilled in the art that the method can be performed in a substantially similar manner using any of the disclosed embodiments without departing from the scope of the present invention.

Although a preferred use of the medical device is to ablate tissue in a patient, the device may also be used on materials other than tissue. In view of the above, it will be seen that the several objects of the invention are achieved.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical device for performing a therapeutic procedure on a patient comprising:
    a body that is removably attachable to a working end of an endoscope, the body having a recess therein;
    an ablating electrode positioned on the body and communicative with an ablating energy source for delivering ablating energy to the electrode when performing the therapeutic procedure on the patient;
    an injection needle positioned in said recess and communicative with a fluid source for delivering fluid to the needle when performing the therapeutic procedure on the patient;
    wherein the ablating electrode is a recess electrode positioned in said recess;
    further comprising a blade slidably disposed within said body and movable between a stored position in which the blade is withdrawn from said recess and a deployed position in which the blade extends into the recess to cut tissue away from the patient; and
    further comprising at least one surface ablating electrode located on an outer surface of the body outside the recess and communicative with said ablating energy source for delivering ablating energy to the at least one surface ablating electrode when performing the therapeutic procedure.

2. A device as set forth in claim 1 wherein the blade is communicative with the ablating energy source for delivering energy to the blade when performing the therapeutic procedure and, during operation of the device, the blade and the at least one surface ablating electrode are oppositely charged.

3. A device as set forth in claim 2 wherein, during operation of the device, the charge on the blade and the at least one surface ablating electrode change with time.

4. A device as set forth in claim 1 wherein said at least one surface ablating electrode includes a first surface ablating electrode and a second surface ablating electrode positioned closer to the recess than the first surface ablating electrode and, during operation of the device, the first and second surface ablating electrodes carry opposite charges.

5. A device as set forth in claim 4 wherein, during operation of the device, the charge on the first and second surface ablating electrodes change with time.

6. A medical device for performing a therapeutic procedure on a patient comprising:
    a body that is removably attachable to a working end of an endoscope, the body having a recess therein;
    an ablating electrode positioned on the body and communicative with an ablating energy source for delivering energy to the ablating electrode when performing the therapeutic procedure on the patient;
    an injection needle positioned in said recess and communicative with a fluid source for delivering fluid to the needle when performing the therapeutic procedure on the patient;
    wherein said ablating electrode is a first surface ablating electrode and the device includes a plurality of surface ablating electrodes including said first surface ablating electrode positioned outside the recess; and
    further comprising a blade slidably disposed within said body and movable between a stored position in which the blade is withdrawn from said recess and a deployed position in which the blade extends into the recess.

7. A device as set forth in claim 6 further wherein the blade is communicative with said energy source for delivering energy to the blade when performing the procedure and, during operation of the device, the blade and at least one of the surface ablating electrodes carry opposite charges.

8. A method for performing a therapeutic procedure on a patient comprising:
    positioning a device body having a recess therein to a desired location within the patient;
    contacting the patient with the device body such that a portion of tissue of the patient becomes disposed within the recess of the device body and at least a tip of an injection needle connected to the device body is embedded below a surface of the tissue of the patient;
    injecting fluid through said needle to a region below the tissue surface;
    ablating the portion of tissue of the patient disposed in the recess by applying energy to the tissue portion through at least one electrode connected to the device body adjacent said recess, wherein, during the ablating step, the application of energy to said tissue portion is through the at least one electrode and the injection needle; and
    further comprising deploying a blade slidably disposed within said body from a stored position in which the blade is withdrawn from said recess to a deployed position in which the blade extends into the recess thereby cutting and containing the tissue disposed within the recess away from the patient.

9. A method as set forth in claim 8 further comprising ablating tissue remaining in the patient after the deploying step.

* * * * *